(12) United States Patent
Malkin et al.

(10) Patent No.: US 11,925,794 B2
(45) Date of Patent: Mar. 12, 2024

(54) CATHETER PUMP SYSTEM AND METHOD OF CONTROLLING A CATHETER PUMP DRIVE

(71) Applicant: PULSECATH B.V., Arnhem (NL)

(72) Inventors: Oren Malkin, Maarssen (NL); Yoram Karmon, Petach Tikva (IL)

(73) Assignee: Pulsecath B.V., Arnhem (NL)

( * ) Notice: Subject to any disclaimer, the term of this patent is extended or adjusted under 35 U.S.C. 154(b) by 391 days.

(21) Appl. No.: 16/756,772

(22) PCT Filed: Oct. 19, 2018

(86) PCT No.: PCT/NL2018/050691
§ 371 (c)(1),
(2) Date: Apr. 16, 2020

(87) PCT Pub. No.: WO2019/078723
PCT Pub. Date: Apr. 25, 2019

(65) Prior Publication Data
US 2021/0187274 A1    Jun. 24, 2021

(30) Foreign Application Priority Data
Oct. 20, 2017   (EP) .................................... 17197608

(51) Int. Cl.
*A61M 60/562*   (2021.01)
*A61M 60/13*    (2021.01)
(Continued)

(52) U.S. Cl.
CPC .......... *A61M 60/414* (2021.01); *A61M 60/13* (2021.01); *A61M 60/139* (2021.01);
(Continued)

(58) Field of Classification Search
CPC .............. A61M 60/562; A61M 60/414; A61M 60/405; A61M 60/148; A61M 60/139
See application file for complete search history.

(56) References Cited

U.S. PATENT DOCUMENTS

| 4,906,229 A | 3/1990 | Wampler |
| 5,833,619 A | 11/1998 | Freed et al. |

(Continued)

FOREIGN PATENT DOCUMENTS

| DE | 102010011998 | 9/2010 |
| EP | 2564883 | 3/2013 |

(Continued)

OTHER PUBLICATIONS

1 Office Action issued for related Indian Application No. 202047017012 dated Aug. 10, 2021, 6 pages.

(Continued)

*Primary Examiner* — Matthew W Schall
(74) *Attorney, Agent, or Firm* — Pearne & Gordon LLP

(57) ABSTRACT

A catheter pump system with a pump having a fluid displacement member in the blood flow channel, a motor and a motor controller having a pressure sensing port for connection to a control pressure source. The motor controller is arranged for causing motor speed to be increased in response to a reduction of pressure applied to the pressure sensing port and for causing motor speed to be reduced in response to an increase of pressure applied to the pressure sensing port. The motor may be a pneumatic motor for driving the pump and the motor controller may be arranged for controlling motor speed by reducing flow through a supply channel to the motor and allowing an increase of flow through the supply channel to the motor in response to control signals received via an input interface.

11 Claims, 3 Drawing Sheets

(51) Int. Cl.
  *A61M 60/139* (2021.01)
  *A61M 60/148* (2021.01)
  *A61M 60/174* (2021.01)
  *A61M 60/205* (2021.01)
  *A61M 60/405* (2021.01)
  *A61M 60/414* (2021.01)
  *A61M 60/554* (2021.01)

(52) U.S. Cl.
  CPC ........ *A61M 60/148* (2021.01); *A61M 60/174* (2021.01); *A61M 60/205* (2021.01); *A61M 60/405* (2021.01); *A61M 60/554* (2021.01); *A61M 60/562* (2021.01); *A61M 2205/3331* (2013.01)

(56) References Cited

U.S. PATENT DOCUMENTS

| | | |
|---|---|---|
| 6,149,578 A | 11/2000 | Downey et al. |
| 2004/0015043 A1* | 1/2004 | Frazier ................ A61M 60/531 600/18 |
| 2004/0034272 A1 | 2/2004 | Diaz et al. |
| 2006/0069299 A1 | 3/2006 | Aboul-Hosn et al. |
| 2013/0085319 A1 | 4/2013 | Evans et al. |

FOREIGN PATENT DOCUMENTS

| | | |
|---|---|---|
| EP | 2851100 | 3/2015 |
| JP | H07265410 | 10/1995 |
| JP | 2000513628 A | 10/2000 |
| WO | 1998/051210 A1 | 11/1998 |

OTHER PUBLICATIONS

Office Action issued for related Japanese Application No. 2020-542522 dated Dec. 8, 2022, 6 pages.

\* cited by examiner

CATHETER PUMP SYSTEM AND METHOD OF CONTROLLING A CATHETER PUMP DRIVE

FIELD AND BACKGROUND OF THE INVENTION

The invention relates to a catheter pump system and to a method of controlling a pump chive of a catheter system.

In various clinical situations, such as when weaning from cardiopulmonary bypass, in the event of cardiogenic shock, insufficiently powerful heart function or acute heart attack, as well as for support during for instance high-risk percutaneous transluminal coronary (balloon) angioplasty, rotoblator procedures, and coronary stent placement, mechanical circulatory support is used to improve the condition of the patient and to increase the likelihood of recovery.

For this purpose, a catheter pump may be used, which pumps blood away from the heart or from closely downstream of the heart. The pump function can be controlled to be pulsatile in synchronization with the beating heart, so that the flow rate at which blood is pumped is increased at the start of systole to support outflow away from the left ventricle and decreased at the start of diastole, so that the outflow of blood during systole is supported and counter pressure encountered by outflowing blood during systole is reduced and contraction of the left ventricle is facilitated.

SUMMARY OF THE INVENTION

It is an object of the present invention to provide a catheter pump for providing pulsatile cardiac support, which is particularly simple and reliable.

According to the invention, this object is achieved by providing a catheter pump system according to claim 1. The invention can also be embodied in a catheter pump system according to claim 8, a method according to claim 10 and in a method according to claim 11.

For providing circulatory support, an intra-aortic balloon pump (IABP), is standard inventory available in virtually every hospital. An IABP is a balloon mounted on a catheter, which is generally inserted into the aorta through the femoral artery in the leg. The balloon is usually guided into the descending aorta to a position at approximately 2 cm from the left subclavian artery. At the start of diastole (when the aortic valve is closed), the balloon is inflated, augmenting coronary perfusion and at the beginning of systole (when the heart ejects blood from the left ventricle through the aortic valve), the balloon is deflated so that the heart can discharge blood more easily. Thereby, overall cardiac output is increased and the left ventricular stroke work and myocardial oxygen requirements are decreased.

Connecting the pressure sensing port of the motor controller to the output port of an IABP driver provides a simple and reliable solution for controlling pulsatile operation of the motor and the pump in sync with pulsations of the heart, such that blood flow out of the heart is supported primarily during systole.

Control of motor speed can also be achieved in a particularly simple, reliable and smooth manner, regardless whether timing signals for the pulsatile operation of the motor and the pump are obtained from an IABP driver output port, if the motor is a pneumatic motor and motor control is achieved in response to control signals by a variable restriction valve reducing flow through the supply channel and allowing an increase of flow through the supply channel in response to control signals received via the input interface.

Particular elaborations and embodiments of the invention are set forth in the dependent claims.

Further features, effects and details of the invention appear from the detailed description and the drawings.

DETAILED DESCRIPTION

Figure 1:
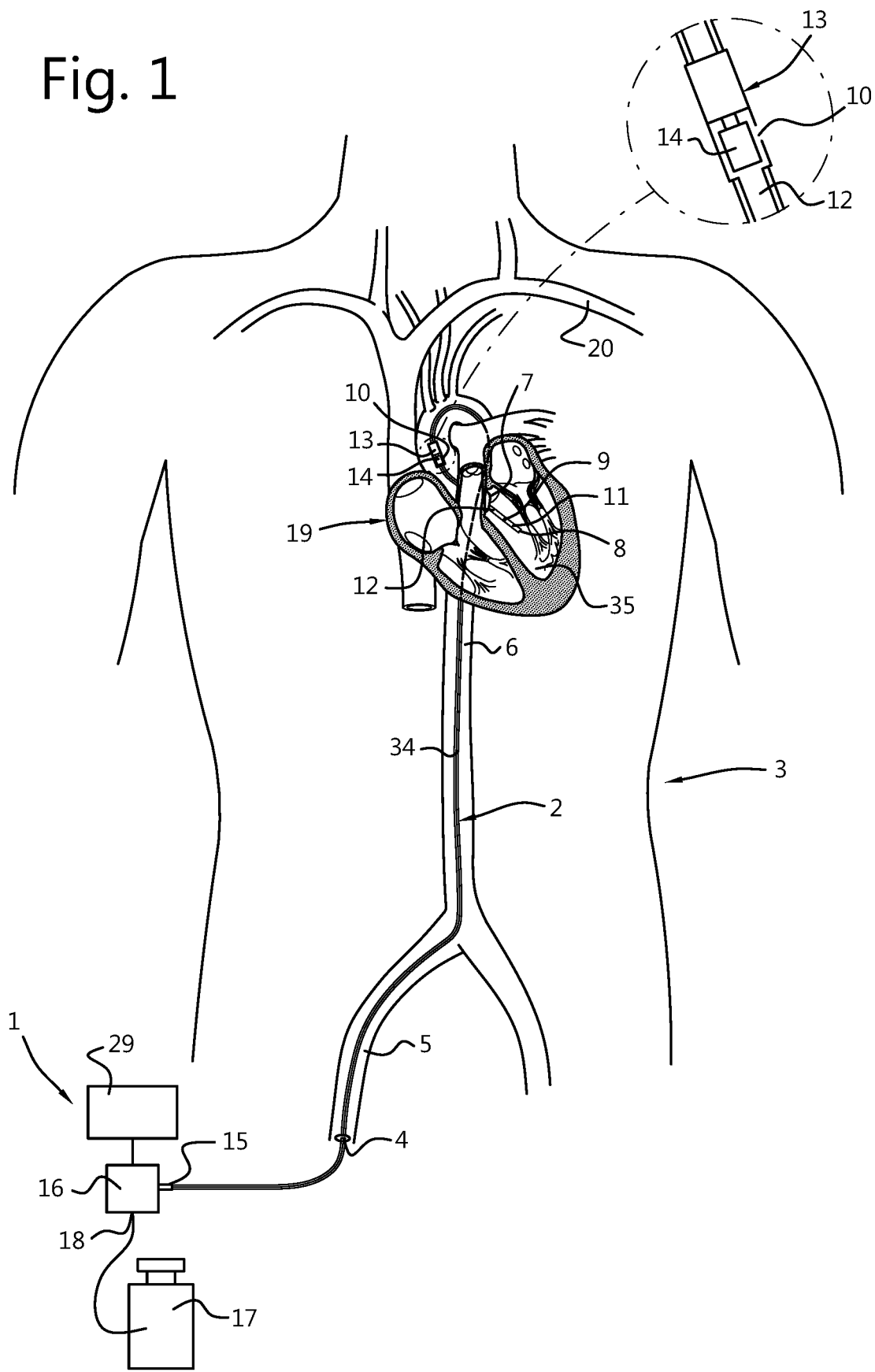
FIG. 1 is a schematic representation of a first example of a catheter pump system according to the invention in operation.
Figure 2:
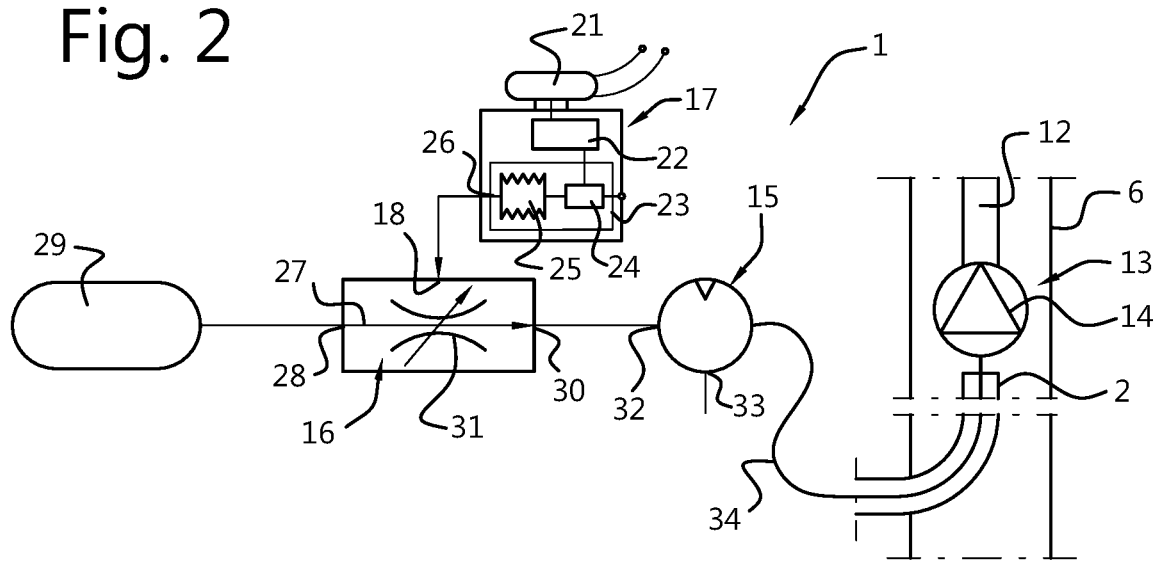
FIG. 2 is a schematic functional representation of the pump system according to FIG. 1.

The invention is first described with reference to the example shown in FIGS. 1 and 2. A catheter pump system 1 according to this example has catheter 2 for insertion into a patient 3. As shown in FIG. 1, the catheter 2 can be brought into a position extending through an opening 4 made in the patient body, an external iliac artery 5 and an Aorta 6 of the patient 3. For bringing the catheter 2 into such a position, it preferably has an insertable length of at least 40 cm (more preferably at least 50 cm) and at most-90 cm (more preferably at most 75 cm). The catheter may for instance be of a 7 to 9 Fr. thickness. Insertion into the aorta via a subclavian artery 20 is also possible. The insertable length can then be shorter e.g. by 10-20 cm. A distal end portion of the catheter 2 is located in a position extending through an aortic valve 7 of the patient 3. In some cases a position of the distal end 8 of the catheter 2 near the aortic valve 7 of the patient 3 can be sufficient. The catheter 2 has an inlet port 9 near the distal end 8 and an outlet port 10 proximally of the inlet port 9. The inlet port may also be located at the distal end of the catheter, but if, as in the present example, the catheter 2 has an end portion 11 that is more flexible than a proximally adjacent section of the catheter 2 and curved for facilitating navigating the catheter tip into position, a position of the inlet port 9 at 1-3 cm from the catheter tip 8 is particularly practical. The outlet port 10 communicates with the inlet port 9 via a blood flow channel 12.

The pump system 1 further includes a pump 13 having a fluid displacement member 14 in the blood flow channel 12 and a motor 15 coupled to the pump 13 for driving the pump 13.

A motor controller 16 is provided for controlling motor speed. The motor controller 16 has a pressure sensing port 18 for connection to a control pressure source 17 which generates a pressure that varies in sync with pulsations of the heart 19. The motor controller 16 is arranged for causing motor speed to be increased in response to a reduction of pressure applied to the pressure sensing port 18 and for causing motor speed to be reduced in response to an increase of pressure applied to the pressure sensing port 18.

In operation, the inlet port 9 is in a left ventricle 35 of the patient 2 or, alternatively, closely downstream of the aortic valve 7 of the patient 2 and the outlet port 10 is downstream of the inlet port 9 and of the aortic valve 7 and communicates with the inlet port 9 via the blood flow channel 12. The motor 16 drives the pump 13 which is coupled to the motor 16. The motor controller 16 controls the speed of the motor 15.

For providing signals to the motor controller 16 on the basis of which timing of speeding up and slowing down of the motor 15 is determined, the source of variable pressure is provided in the form of an IABP driver 17. Such IABP drivers 17 are commonly available in hospital departments involved in the treatment of cardiac dysfunction and have a detector 21 detecting diastole and systole of the patient's heart from for instance an electrocardiogram, blood pressure or a pacemaker signal. The IABP driver 17 further has a pressure controller 22, a pressure source 23, a balloon port 26 in fluid communication with the pressure source 23 and for connection to an intra aortic balloon. In this example, the pressure source 23 includes a linear actuator 24 and a bellows 25 coupled to the actuator 24, so that the bellows 25 is expanded and compressed when the actuator 24 retracts and, respectively, expands. The interior of the bellows 25 communicates with balloon port 26 so that pressure applied to the balloon port 26 varies cyclically if the bellows 25 is reciprocally expanded and compressed. Other mechanisms for applying a variable pressure to the balloon port are also conceivable, but not described since IABP drivers are standard hospital equipment. The pressure controller 22 and the pressure source 23 of the IABP driver 17 according to this example are arranged for generating a balloon inflation pressure at the start of diastole and removing or at least reducing balloon inflation pressure at the start of systole as is illustrated by the IABP pressure curve in FIG. 5.

The motor controller 16 has a pressure sensing port 18 in fluid communication with the balloon port 26, so that the pressure applied to the pressure sensing port 18 varies in unison with the pressure applied to the balloon port 26. The motor controller 16 is arranged for causing the speed of the motor 15 to be increased in response to a reduction of pressure applied to the pressure sensing port 18 and for causing the speed of the motor 15 to be increased in response to a reduction of the pressure applied to the pressure sensing port 18. Thus, as is illustrated by the 'Pump Flow Rate' curve in FIG. 5, the pump flow rate increases if IABP pressure decreases and vice versa.

In this embodiment and other embodiments, a certain shift (towards in advance or as a delay) in the response of the pump flow rate variation to the IABP pressure variation may occur. The shift is preferably less than a quarter and more preferably less than an eighth of a full cycle.

In the present example, the motor 15 is a pneumatic motor and the motor controller 16 has a supply channel 27 extending through the motor controller 16 between an inlet 28 for connection to a pressure source 29 and an outlet 30 in fluid communication with the motor 15. A variable restriction valve 31 is arranged for reducing flow through the supply channel 27 in response to an increase of pressure applied to the pressure sensing port 18 and for allowing an increase of flow through the supply channel 27 in response to a reduction of pressure applied to the pressure sensing port 18. This allows control of motor speed to be achieved in a particularly simple, reliable and smooth manner.

The motor 15 and the pump 13 are arranged for operation at a pressure difference between an inlet 32 and an outlet 33 of the motor 15 of at least 2 bars at a flow rate of at least 30 l/min (more preferably at least 2.5 bar at a flow rate of at least 40 l/min). Because an IABP driver is typically not capable of supplying such a pneumatic power, the pneumatic pressure is supplied to the motor controller 16 from a pressure source 29 that has been provided in addition to the IABP driver 17.

The motor 15 is coupled to the pump 13 via a flexible drive shaft 34 extending through a lumen of the catheter 2 so that the motor 15 can drive the pump 13 via the flexible drive shaft 34. This allows the motor 15 to be located outside of the body 3 of the patient, i.e. proximally of an opening 4 made in the body 3 of the patient. Locating the motor 15 outside the body 3 of the patient is advantageous for safety reasons, because in the event of a leak in a portion of the catheter inside the patient's body 3, pressurized air would be injected into the blood of the patient. Such dangers can be reduced by using helium as a driving gas, but that would increase operating costs and complexity and still a larger leak would constitute a substantial hazard.

To ensure effective discharging of blood out of the left ventricle, the inlet port 9 and the outlet port 10 are at a mutual distance of at least 5 cm and more preferably at least 6 cm. This distance is preferably less than 10 cm.

To avoid disturbing expansion of the left ventricle during diastole, the motor controller 16, the motor 15 and the pump 13 are arranged for varying flow rate generated by the pump 13 from a lowest flow rate of less than 3 l/min at a difference between pressure at the outlet port 10 and pressure at the inlet port 9, as a result pumping action of the heart and the pump 13, of 80-120 mmHg.

For effectively supporting the discharging of blood out of the left ventricle during systole, the motor controller 16, the motor 15 and the pump 13 are arranged for causing the flow rate generated by the pump 13 to reach a highest flow rate of at least 4 l/min (and more preferably at least 5 l/min) at a difference between pressure at the outlet port and pressure at the inlet port 9, as a result pumping action of the heart and the pump 13, of 15-90 mmHg.

Figure 3:
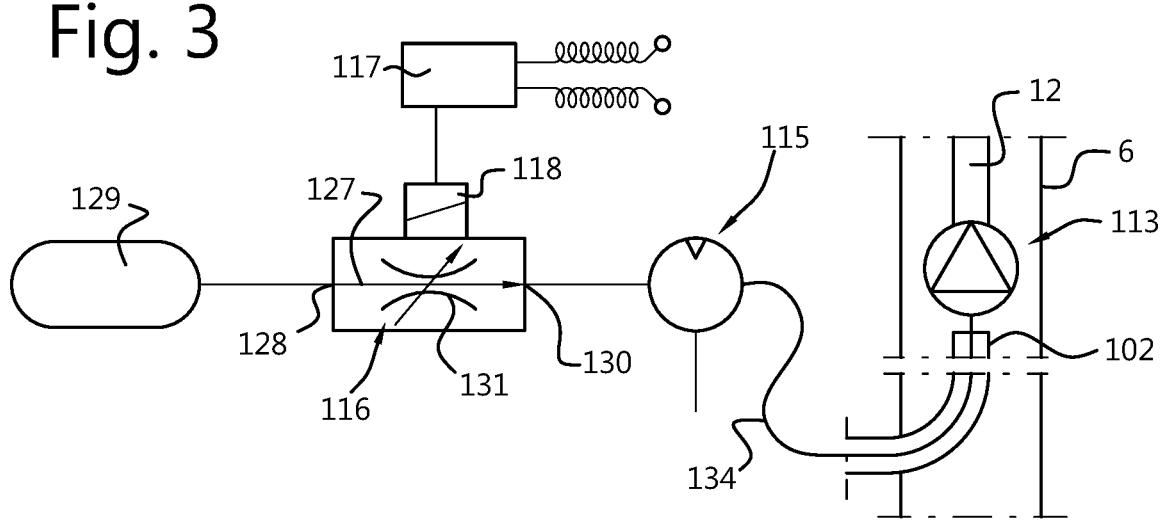
FIG. 3 is a schematic functional representation of a second example of a pump system according to the invention.

In another embodiment, shown in FIG. 3, a catheter pump system includes a catheter 102 for insertion into a patient 3 into a position extending through the aorta 6 of the patient's body 3. As in the embodiment described above, a pneumatic motor 115 is provided for driving the pump 113 and a flexible drive shaft 134 extends through a lumen of the catheter 102. The drive shaft 134 couples the pump 113 to the motor 115 so that the pump 113 can be driven by the motor 115. The motor controller 116 for controlling motor speed has a supply channel 127 extending through the motor controller 116 between an inlet 128 for connection to a pressure source 129 and an outlet 130 in fluid communication with the motor 115. A variable restriction valve 131 is arranged for controlling flow through the supply channel 127 and an input interface 118 is provided for inputting control signals. The variable restriction valve 131 is arranged for reducing flow through the supply channel 127 and allowing an increase of flow through the supply channel 127 in response to control signals received via the input interface 118. The input interface 118 can for instance be connected to an apparatus 117 for sensing cardiac signals, such as an ECG (electrocardiogram) device, to a blood pressure transducer at or near the distal tip of the catheter or to a pacemaker.

In operation, the motor controller 116 receives control signals via the input interface 118 and the variable restriction valve 131 is operated for reducing flow through the supply channel 127 and allowing an increase of flow through the supply channel 127 in response to the control signals received via the input interface 118.

Figure 4:
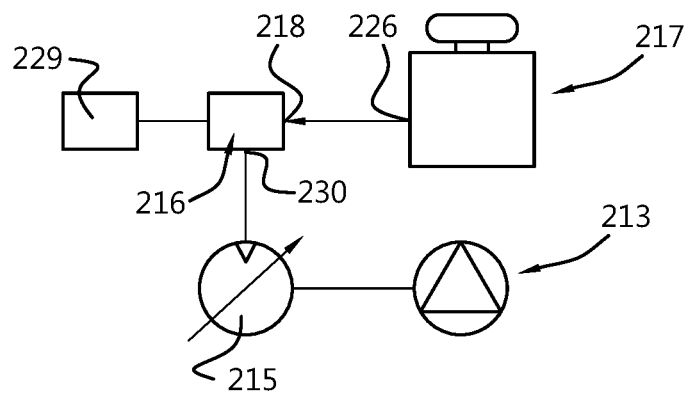
FIG. 4 is a schematic functional representation of a third example of a pump system according to the invention.

In FIG. 4, a further example of a catheter pump system according to the invention is shown. In this system, a motor controller control 216 is coupled to the balloon port 226 of an IABP driver 217 and to an electric power source 229. The motor 215 is a variable speed electric motor 215 and is coupled to a power output 230 of the motor controller 216 so that electric power can be supplied to the motor 215 under control of the motor controller 216. The motor controller 216 further has a pressure sensing port 218 coupled to a balloon port 226 of the IABP driver 217, so as to receive pressure outputted by the IABP driver 217. The motor 215 is coupled to the pump 213 for driving the pump. In this example, the motor 215 is arranged close to the pump 213 in a distal end portion of the catheter, i.e. inside the patient when in operation.

Figure 5:
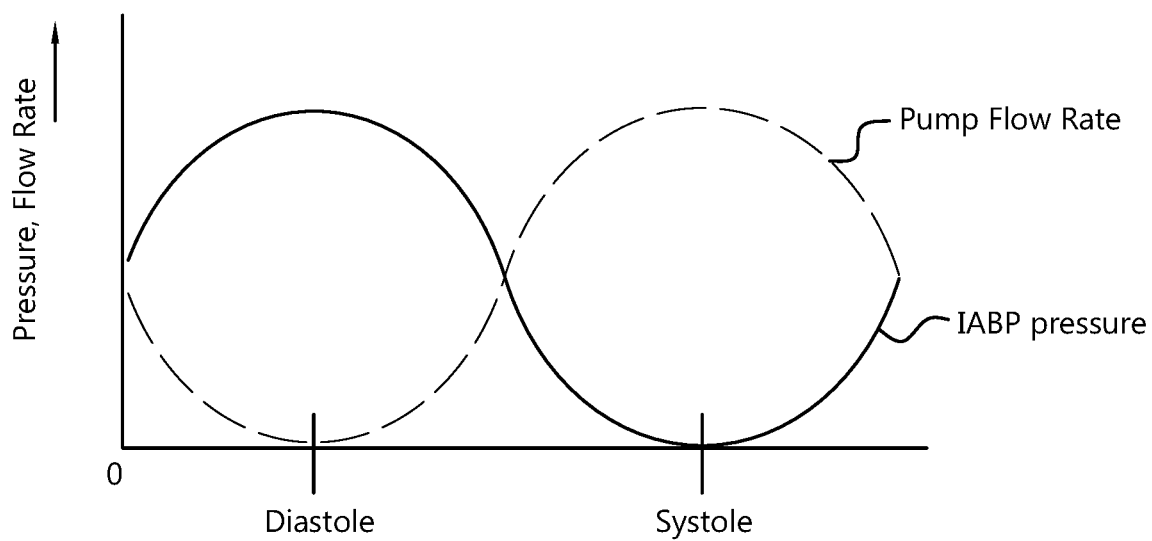
FIG. 5 is a graph showing the relationship between IABP driving pressure and pump flow rate of an example of pump system according to the invention.

In operation, the motor controller 216 controls power supply to the motor 215 so that, in response to pressure variations applied to the pressure sensing port 218 by the IABP driver 217, the motor speed increases in response to a reduction of pressure applied to the pressure sensing port 218 and the motor speed reduces in response to an increase of pressure applied to the pressure sensing port 218, in a manner as is illustrated by FIG. 5. Also in this embodiment, a certain time shift (advance or delay) between maximum IABP pressure and minimal flow rate generated by the pump 213 as well as between minimal IABP pressure and maximal flow rate generated by the pump 213 may occur. Such a time shift may be constant or vary over the cycle of pressure increase and reduction.

Several features have been described as part of the same or separate embodiments. However, it will be appreciated that the scope of the invention also includes embodiments having combinations of all or some of these features other than the specific combinations of features embodied in the examples.

The invention claimed is:

1. A catheter pump system comprising:
   a catheter for insertion into a patient into a position extending through an aorta of the patient such that a distal end portion of the catheter can be located near or extend through an aortic valve of the patient, the catheter having an inlet port at or near a distal end and an outlet port proximally of the inlet port and communicating with the inlet port via a blood flow channel;
   a pump having a fluid displacement member in the blood flow channel that provides communication between the inlet port and the outlet port;
   a motor coupled to the pump for driving the pump;
   a motor controller for controlling motor speed, the motor controller having a pressure sensing port for connection to a control pressure source, the motor controller being arranged for causing motor speed to be increased in response to a reduction of pressure applied to the pressure sensing port and for causing motor speed to be reduced in response to an increase of pressure applied to the pressure sensing port.

2. A pump system according to claim 1, wherein the motor is a pneumatic motor and wherein the motor controller has:
   a supply channel extending through the motor controller between an inlet for connection to a pressure source and an outlet in fluid communication with the motor,
   a variable restriction valve arranged for reducing flow through the supply channel in response to an increase of pressure applied to the pressure sensing port and for allowing an increase of flow through the supply channel in response to a reduction of pressure applied to the pressure sensing port.

3. A pump system according to claim 2, wherein the motor and the pump are arranged for operation at a pressure difference over the motor of at least 2 bar.

4. A pump system according to claim 1, wherein the motor is coupled to the pump via a flexible drive shaft extending through the catheter.

5. A pump system according to claim 1, wherein the inlet port and the outlet port are at a mutual distance of at least 5 cm.

6. A pump system according to claim 1, wherein the motor controller, the motor and the pump are arranged for varying flow rate generated by the pump from a lowest flow rate of less than 3l/min at a difference between pressure at the outlet port and pressure at the inlet port of 80-120 mmHg.

7. A pump system according to claim 1, wherein the motor controller, the motor and the pump are arranged for varying flow rate generated by the pump up to a highest flow rate of at least 4l/min at a difference between pressure at the outlet port and pressure at the inlet port of 15-90 mmHg.

8. A catheter pump system comprising:
   a catheter for insertion into a patient into a position extending through an aorta of the patient such that a distal end portion of the catheter can be located near or extend through an aortic valve of the patient, the catheter having an inlet port at or near a distal end and an outlet port proximally of the inlet port and communicating with the inlet port via a blood flow channel;
   a pump having a fluid displacement member in the blood flow channel;
   a pneumatic motor for driving the pump;
   a flexible drive shaft extending through the catheter, the drive shaft coupling the pump to the motor;
   a motor controller for controlling motor speed, the motor controller having:
   a supply channel extending through the motor controller between an inlet for connection to a pressure source and an outlet in fluid communication with the motor,
   a variable restriction valve connected and arranged for controlling flow through the supply channel, and
   an input interface for inputting control signals to the motor controller;
   wherein the variable restriction valve is arranged for reducing flow through the supply channel and allowing an increase of flow through the supply channel in response to control signals received via the input interface.

9. A catheter pump system according to claim 8, wherein the input interface is in the form of a pressure sensing port for connection to a control pressure source, the motor controller being arranged for causing motor speed to be increased in response to a reduction of pressure applied to the pressure sensing port and for causing motor speed to be reduced in response to an increase of pressure applied to the pressure sensing port.

10. A pump system according to claim 1, wherein the pressure sensing port of the motor controller is in fluid communication with the control pressure source, such that the pressure applied to the pressure sensing port varies in unison with the pressure applied to a balloon port.

11. A pump system according to claim 10, wherein the control pressure source is an intra aortic balloon pump driver.

* * * * *